United States Patent [19]

Sachs

[11] 3,965,889

[45] June 29, 1976

[54] APPARATUS FOR THE SAMPLING OF BLOOD AND THE SEPARATION OF PLASMA UNDER ANAEROBIC CONDITIONS

[75] Inventor: Charles E. Sachs, Paris, France

[73] Assignee: Commissariat a l'Energie Atomique, Paris, France

[22] Filed: Jan. 3, 1975

[21] Appl. No.: 538,270

Related U.S. Application Data

[63] Continuation-in-part of Ser. No. 308,940, Nov. 24, 1972, abandoned.

[30] Foreign Application Priority Data

Nov. 26, 1971  France .......................... 71.42350

[52] U.S. Cl. ............................. 128/2 F; 23/292; 128/276; 128/DIG. 5; 233/1 R; 233/26
[51] Int. Cl.² .................................. A61B 10/00
[58] Field of Search ........... 128/2 F, DIG. 5, 214 D, 128/276, 216, 272, 275; 233/26 TR; 23/258.5, 292

[56] References Cited

UNITED STATES PATENTS

| | | | |
|---|---|---|---|
| 2,855,933 | 10/1958 | Erikson | 128/272 |
| 2,999,500 | 9/1961 | Schurer | 128/276 |
| 3,032,037 | 5/1962 | Huber | 128/276 |
| 3,185,154 | 5/1965 | Caccavo et al. | 233/26 X |
| 3,189,227 | 6/1965 | Hobbs et al. | 222/94 |
| 3,486,539 | 12/1969 | Jacuzzi | 128/272 X |
| 3,545,671 | 12/1970 | Ross | 128/272 X |
| 3,648,698 | 3/1972 | Doherty | 128/276 |
| 3,660,033 | 5/1972 | Schwartz | 128/DIG. 24 |
| 3,750,645 | 8/1973 | Bennett et al. | 233/26 X |

FOREIGN PATENTS OR APPLICATIONS 1,036,000    7/1966    United Kingdom ................. 128/2 F Primary Examiner—Kyle L. Howell
Attorney, Agent, or Firm—Cameron, Kerkam, Sutton, Stowell & Stowell

[57] ABSTRACT

Blood is withdrawn from a patient for ultimate centrifuging into plasma and erythrocytes by mounting a supple substantially non-extensible under conditions of use thermosealable walled container in a carrier, the container having a top provided with an orifice closed by a rubber washer. A needle is mounted in a hollow cap sized to receive the carrier. The needle is inserted in the vein by pressing the carrier into the cap which also causes the needle to perforate the washer. A vacuum is drawn on the carrier drawing blood into the container, the container having a medial restriction dividing the container into two equal chambers. After filling, the container is withdrawn from the cap before removal of the needle from the vein and the container is mounted in a second carrier which is closed by the cap. The blood is then centrifuged, the plasma collects in the chamber above the restriction and the erythrocytes collects in the chamber below the restriction. The container is then separated at the restriction and the separated chambers sealed on separation.

4 Claims, 4 Drawing Figures

APPARATUS FOR THE SAMPLING OF BLOOD AND THE SEPARATION OF PLASMA UNDER ANAEROBIC CONDITIONS

REFERENCE TO RELATED APPLICATION

This application is a CIP of my application Ser. No. 308,940, filed Nov. 24, 1972, now abandoned.

BACKGROUND OF THE INVENTION

The present invention has for its object a process and apparatus for obtaining blood plasma handled and conserved in anaerobic conditions for medical analysis.

Its principal object is to make possible the three following steps without the sample of blood being in contact with the ambient air:

1. Taking a sample of blood from the vein of a patient in a container holding an anti-coagulant.
2. Separation by centrifugation of the erythrocytes.
3. Division of the parts of the container holding the erythrocyte and plasma phases.

The apparatus in accordance with the invention avoids the inherent inconveniences of known methods: mixture of oil with the plasma and itroduction of oil in the measuring devices as in the classic method of sampling with mineral oil; initial degassing and impossibility of extraction of the plasma separated from the erythrocytes under strict anaerobic conditions as in the method utilizing sampling tubes under vacuum such as a "Vacutainer".

The object of the present invention is an apparatus for the sampling of blood and the separation of the plasma under totally anaerobic conditions which avoids all of the inconveniences of apparatus of the prior art.

SUMMARY OF THE INVENTION

Apparatus in accordance with the present invention is pricipally characterized by and comprises:

A container with transparent and supple substantially non-extensible under conditions of use thermosealable walls which can be inflated or flattened if under vacuum or under pressure comprising two distinct chambers of substantial equal size connected by a restricted passage and a rigid top connected to the container at one of its extremities, the top having a central opening for communication with the exterior closed by an elastic rubber sealing washer located in a seat in the top across the opening, the top having a screw thread on its external lateral face.

A first rigid transparent carrying and receiving tube having at its upper part an orifice receiving the top and having a screw thread cooperating with the screw thread on the top in such a way as to support the container therein, the first rigid tube icluding an opening for communication with the exterior.

A second rigid transparent receiving and carrying tube having at its upper part an opening receiving the top and having a screw thread cooperating with the screw thread of the top in such a way as to support the condtainer therein.

In accordance with an important characteristic of the present invention, the supple substantially non-extensible under conditions of use thermosealable transparent walled container to receive the blood of the patient is made of thermosealable plastic material. This permits an easy manufacturing of the container from a cylindrical tube in which there has been formed at about midheight a central restriction by thermopressing of a part of the walls of the cylinder. The lower extremity of the tube is also closed and sealed by thermopressing and its upper extremity is secured in the same way to the top for the container. This provides on one side and the other of the central restriction two separate chambers of substantial equal volume which are utilized later to receive separately, after centrifugation, the plasma separated from the erythrocytes. The flexible walled container can thus take two different forms, that is, an inflated form in which upper and lower separated chambers have maximum volume and a flattened form when under external pressure, with the walls of the container then pressed together. This arrangement makes the use of this container very easy because of the supple non-extensible thermosealable walls which, according to whether the container is under exterior pressure or under exterior vacuum, adopt an inflated form or a flattened form.

Another equally important characteristic of the apparatus of the present invention is that the rigid top closing the supple non-extensible thermosealable walled container at its upper end includes a space of small volume which when placed under vacuum during fabrication retains a small bubble of air or of a neutral gas such as nitrogen. This is necessary for two essential reasons, namely, to avoid during later use of the apparatus penetration by the needle of the walls of the container and the presence of such a bubble is absolutely indispensable to permit internal movement of the liquid taken from the vein of the patient within the container for a good mixing of the sample with the anticoagulant by turning and agitating the container to obtain the indispensable homogenization of the sample with the anticoagulant, the anticoagulant being placed in the container before taking the blood sample.

The present invention also has for an object a process of use of the apparatus of the present concept for the sampling of blood of a patient and the separation of the plasma from the erythrocytes comprising the following successive steps:

A supple non-extensible thermosealable walled container provided with a top is screwed in a first container carrying tube.

A neelde with two beveled ends is inserted in the vein of the patient, this needle being supported by a needle support in the form of a protective cap and the first container carrying tube is pushed as a syringe piston into the needle support to the bottom thereof which causes perforation by the needle of the elastic washer of the top.

The first container carrying tube is then placed under vacuum by connecting its oening communicating with the exterior to a source of vacuum which causes withdrawal of blood from the patient into the supple non-extensible thermosealable walled container with inflation of the two chambers.

The first container carrying tube is withdrawn, the supple walled container is unscrewed therefrom and is placed in a second container carrying tube.

The sample of blood is centrifuged and the supple non-extensible thermosealable walled container is unscrewed and removed from the second container carrying tube.

The supple substantially non-extensible under conditions of use thermosealable walled container is then divided by heated cutters at the medial restriction exactly at and just above the level of the plasma-erythrocyte interface, to separate and seal the two chambers containing, respectively, the plasma and the erythrocytes.

BRIEF DESCRIPTION OF THE ACCOMPANYING DRAWINGS

The present invention will be better understood from the following description of a preferred embodiment thereof for the sampling of blood and separation of plasma. This description will refer to the accompanying drawings, in which like reference characters indicate like parts, and in which FIG. 1 shows a supple non-extensible thermosealable walled container provided with a rigid top screwed in the second container carrying tube;

DESCRIPTION OF THE PREFERRED EMBODIMENT

Figure 1:
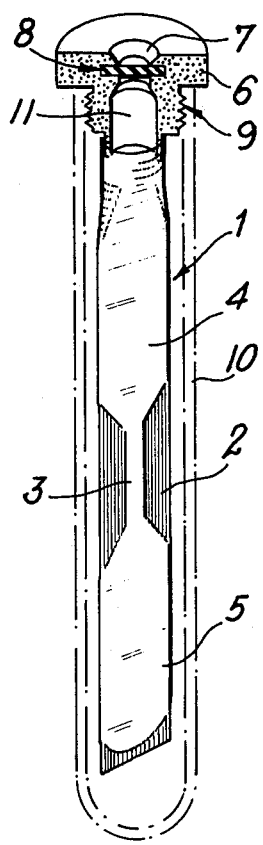

Referring now to FIG. 1, the supple non-extensible thermosealable walled container 1 of thermosealable plastic material provides for movement of the walls under pressure or vacuum. Container 1 is made from a cylindrical tube which has been restricted by thermosealing of the walls at 2 in the medial zone to provide a restriction 3 placing the upper chamber 4 thereof in communication with lower chamber 5. Container 1 is closed at its top by rigid plastic top 6 having an opening 7 closed by a rubber washer 8. In FIG. 1, container 1 and top 6 are screwed at 9 in a closed receiving and carrying tube 10 of the second type. In tube 10 of FIG. 1, which is that in which the supple non-extensible thermosealable walled container may be sold in commerce, a relatively strong vacuum has been drawn in chambers 4 and 5 and container 1 is totally flattened except at its upper part where there is located, primarily in space 11 of top 6, a small bubble of air indispensable to proper functioning of the structure, as will be explained hereinafter.

Figure 2:
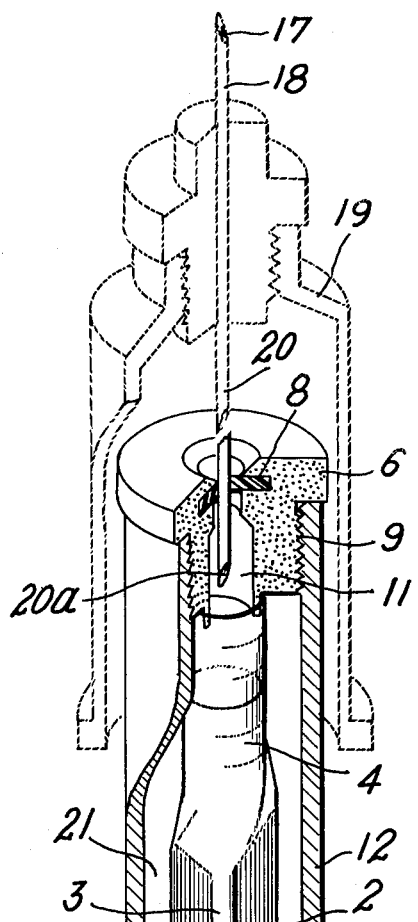
FIG. 2 shows the supple non-extensible thermosealable walled container connected by its top screwed in the first container carrying tube, the assembly being pierced by a sampling needle having two beveled ends mounted in a needle carrier having the form of a protective cap.
Figure 2:
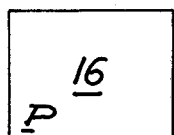
Figure 3:
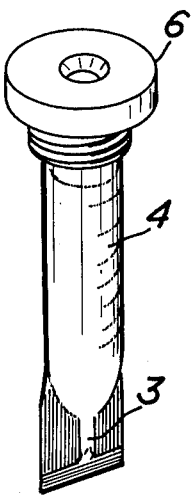
FIG. 3 shows the supple non-extensible thermosealable walled container filled with withdrawn blood mounted in a container carrying tube of the second type.

For use of the container, seen in FIG. 2, the supple non-extensible thermosealable walled container 1 is first separated from the receiving and carrying tube 10 by unscrewing top 6 and subsequent introduction thereof, as seen in FIG. 1, in a first container carrying tube 12 in which the top 6 is screwed at the top thereof. The first container carrying tube 12, in accordance with the present invention, has an opening 13 for communication with the exterior through a flexible rubber tube 14 and a valve 15 for communication with a vacuum pump 16.

To obtain a sample of blood by the apparatus of FIG. 2, the following procedure is carried out. The beveled end 17 of a needle 18 is introduced into the vein of a patent, not shown in the drawings, and needle 18 is supported by a needle carrier 19 in the form of a protective cap of known type. This assembly of needle 18 and protective cap 19 is shown in FIG. 2 in broken lines. Once end 18 of the needle is introduced into the vein of the patient, the upper part of the second container carrying tube 12 is pushed into protective cap 19 of the needle carrier as if a syringe piston. During this step, the second beveled end 20 of needle 18 perforates washer 8 of top 6 and enters space 11 in the central part of top 6. Practically, the part of needle 18 which is in the protective cap has a length such that when second tube 12 is totally introduced into cap 19, the extremity 20 of the needle is in position 20a, shown in solid lines in FIG. 2, and in the lower part of space 11. It is obviously necessary during introduction of needle 18 into top 6 not to perforate the supple non-extensible thermosealable walls of container 1.

These several steps having been carried out, pump 16 is started and valve 15 is opened which causes a slight vacuum in space 21 within the first container carrying tube 12 causing inflation of chambers 4 and 5 of flexible container 1, together with introduction therein of blood from the patient through needle 18. It is seen that this occurs without any contact of the blood with the environmental atmosphere.

When sampling of the blood is completed, the source of vacuum 16 is disconnected by closing valve 15 and container 1 is then placed under atmospheric pressure by disconnecting tube 14. The second container carrying tube 12 is then removed during which needle 18 is withdrawn from the vein of the patient.

The flexible wall container 1 is filled with sampled blood and is then again inserted into a container carrying tube 10 of the second type. The blood is then centrifuged and plasma collects in chamber 4 of tube 1 while the erythrocytes are deposited by sedimentation in lower chamber 5 of tube 1. Container 1 is then carefully removed from the container carrying tube 10, used during centrifuging, to avoid return into suspension of the separated erythrocytes. The supple non-extensible thermosealable walled container is then divided by heated cutters both separating and thermally sealing the cut extremities. Division is carried out in the restricted zone 3 a little above the interface plasma-erythrocytes as in FIG. 4. The plasma is thus separated from the erythrocytes under strictly anaerobic conditions. Upper chamber 4 of container 1 contains the plasma for further use and is protected by simply screwing it in a receiving and carrying tube of the second type similar to tube 10 but of reduced length.

Figure 4:
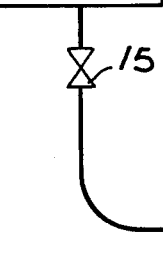
FIG. 4 shows, after centrifuging, cutting and thermal sealing the upper chamber of the supple non-extensible thermosealable walled container filled with plasma.

The apparatus and process above described has certain important advantages with respect to known techniques, among which can be noted that, during sampling, the blood is withdrawn by vacuum but without the atmosphere coming in contact with the blood; the vacuum utilized can be controlled and because of this a practically constant moderate negative pressure can be used. This avoids all degassing and particularly in the initial stages of sampling. Control of the vacuum also controls the amount of blood from the vein and this can be decreased, stopped or increased by simple manipulation of valve 15 in tube 14. The top is of resistant plastic material and provides a small space in its center for a small volume or bubble of gas. This volume is sufficiently small to avoid any significant loss of gas. This bubble is of extreme importance because it provides for a good mixing of the sample by oscillation of the container for homogenization and distribution of the anticoagulant. The lower extremity of the needle cannot extend beyond the lower part of the top which protects the flexible wall of the container against poor handling which might otherwise perforate the wall. Removal of successive samples of plasma from the upper chambers of the container, as seen in FIG. 4, can be carried out without causing negative pressure in the separated chamber. During aspiration with a needle connected to a syringe and passing through the rubber washer, the elastic walls of the chamber progressively drawn together and the plasma in chamber 4 thus remains constantly at atmospheric pressure.

What I claim is:

1. Apparatus for the sampling of blood and the separation of plasma under anaerobic conditions comprising a transparent supple substantially non-extensible under conditions of use thermosealable walled container which can be inflated or flattened if under exterior vacuum or pressure, two separate substantially equal chambers in said container, a restriction connecting said two chambers, an open end for said container, a rigid top connected to said container at said open end, a central orifice in said top, an elastic washer closing said top mounted across said orifice, a screw thread on the external face of said top, a rigid container carrying tube, a bottom and an open end for said tube, a second orifice in the open end of said tube receiving said top, a screw thread in said second orifice receiving the screw thread of said top to mount said supple substantially non-extensible thermosealable walled container in said tube, and an opening in said tube adapted to communicate with a source of vacuum.

2. Apparatus as described in claim 1, said supple walled container being of plastic material.

3. Apparatus as described in claim 2, said transparent supple substantially non-extensible under conditions of use thermosealable walled container being a cylindrical tube having a central restriction at about midlength, the walls of said cylinder being thermosealed together forming said restriction, the lower end of said cylinder being closed by thermosealing and the upper end of said cylinder being thermosealed to said top.

4. Apparatus as described in claim 1, including a central small volume space in said top and a bubble of a neutral gas such as nitrogen in said space.

* * * * *